US00H002242H

(19) United States
(12) Statutory Invention Registration
Gonzales

(10) Reg. No.: US H2242 H
(43) Published: Jul. 6, 2010

(54) LIGHT THERAPY SYSTEM

(76) Inventor: George Gonzales, 425 N. Gardner St., Los Angeles, CA (US) 90036

(21) Appl. No.: 11/373,782

(22) Filed: Mar. 9, 2006

Related U.S. Application Data

(60) Provisional application No. 60/774,454, filed on Feb. 17, 2006.

(51) Int. Cl.
*A61N 5/06* (2006.01)

(52) U.S. Cl. ..... 607/88

(58) Field of Classification Search ..... 607/88
See application file for complete search history.

(56) References Cited

U.S. PATENT DOCUMENTS 6,663,659 B2 * 12/2003 McDaniel ..... 607/88

* cited by examiner

*Primary Examiner*—Michelle Clement
(74) *Attorney, Agent, or Firm*—John D. Titus

(57) ABSTRACT

An apparatus for treating musculoskeletal disorders comprises a plurality of light emitting diodes and a control circuit. The control circuit causes the light emitting diodes to pulse at predetermined frequencies of from 0 (continuous) to 125 Hz. The light emitting diodes themselves emit light radiation in a frequency range of 628 nanometers (+/− 5%) for the visible diodes and 850 nanometers (+/− 5%) for the infrared diodes.

1 Claim, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

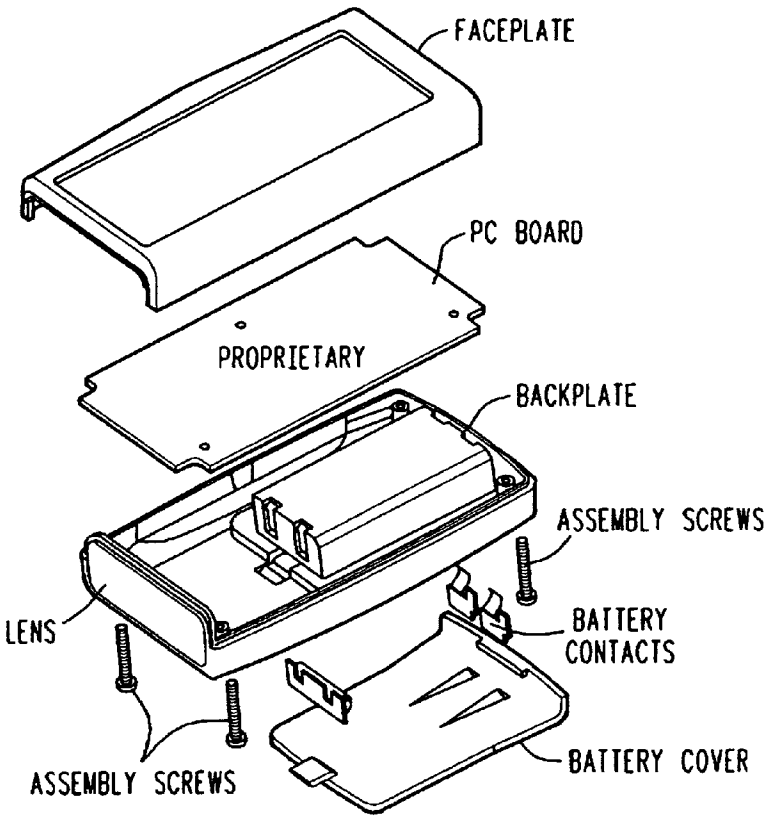
FIG. 2
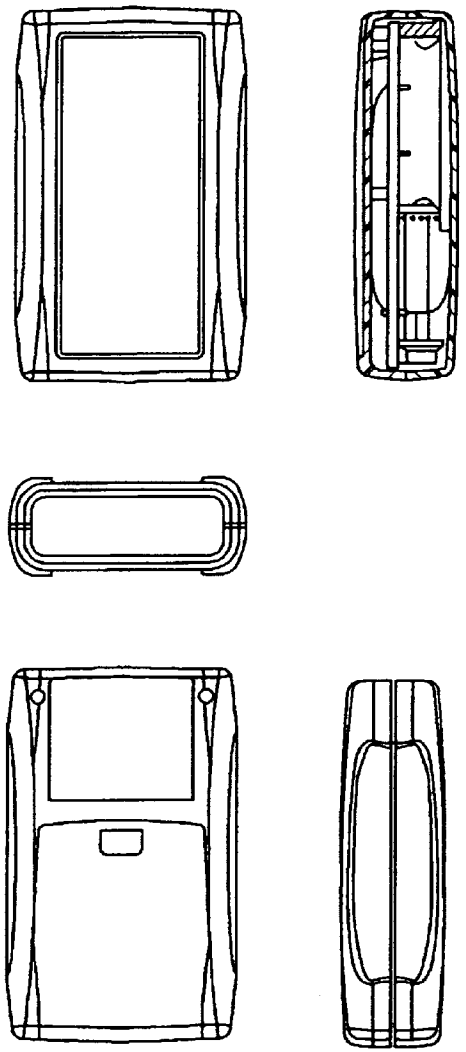

LIGHT THERAPY SYSTEM

CROSS-REFERENCE TO RELATED APPLICATION

This application claims benefit of priority of U.S. provisional application number 60/774,454 filed on Feb. 17, 2006.

BACKGROUND OF THE INVENTION

The GRT LITE Model PRO-8 A is substantially equivalent to other pulsed therapeutic light therapy systems currently in commercial distribution. The Model PRO-8A has the same intended use and similar technological characteristics to predicate devices. It combines the clinically accepted therapeutic uses of several previously FDA 510(k) approved light therapy systems currently in commercial distribution into one compact system.

The technological equivalence to the predicate devices is substantiated by the wavelength and power output generated by the Model PRO-8A. The Model PRO-8A will provide the same treatment benefits and regimens for clinical presentations already approved by the Food and Drug Administration for the predicate devices.

The predicate devices the Model PRO-8A establishes equivalence to include:

| Predicate Device | 510(k) if | Manufacturer |
|---|---|---|
| Tuco Erchonia PL3000 | KO 12580 | Tuco Innovations |
| Excalibur System | K041530 | Stargate International, Inc. |
| Microlight 830 Laser | K010175 | Microlight Corporation of America |
| Acculaser Pro LLLT Device | K020657 | Acculaser, Inc. |

The GRT LITE Model PRO-8A is a non-heating lamp, infrared as described under the provisions of 21CFR §890.5500 and is clinically indicated for:

Adjunctive use in providing temporary relief of minor chronic neck and shoulder pain of nisculoskeletal origin.

Adjunctive use in providing temporary relief of minor chronic pain associated with Carpal Tunnel Syndrome (CTS).

As with the predicate devices, pain therapy treatment can be prescribed for pain associated with the clinical presentations specified above by having the beams pulsed or continuous with time considerations. The GRT LITE Model PRO-8A's variables conform to the performance specifications of the clinical parameters used by the predicate devices in wavelength, frequency as a function of time, and power output.

BRIEF DESCRIPTION OF THE DRAWINGS

FIG. 2 is an exploded perspective and machine drawing views of the housing of the GRT light apparatus.

DETAILED DESCRIPTION

The Model PRO-8A is a hand-held, non-invasive, pain therapy system which utilizes four nonheating light emitting diodes (LED) consisting of two visible LED's and two infrared LED's in one system, It combines the clinically accepted therapeutic treatment of numerous predicate light therapy systems currently in commercial distribution and 510(k) approved.

The system consists of a basic hand-held, battery operated, control unit with the four LED's emitting light through a special red acrylic lens which does not absorb any light transmission. The visible LEDs operate at a measured wavelength of 628 nm (±5%) and the infrared LEDs operate at a measured wavelength of 850 nm (±5%), The Model PRO-8A complies with all performance, labeling, and manufacturing standards set forth in 21 CFR.

The GRT LITE Model PRO-8A and the aforementioned predicate devices emit visible and invisible photonic energy to human tissue. The comparing of the technologies is dependent on the laws of physics in that the variables are frequency, wavelength, power output, and time.

The performance parameters and intended use of the GRT LITE Model PRO-8A are identical to all predicate devices and conforms with all FDA approved application protocols for the devices.

The testing of the Model PRO-8A includes functional performance, electrical safety, and component specification verification This includes an eight-stage manufacturing testing and verification GRT Solutions, Inc. procedure protocol that is tracked by run component and system serial number.

The operation of the Model PRO-8A is controlled using PROM technology. Once the CPU is programmed, the "hard software" cannot be changed or altered. This hard software affords the operator six different selection options for the Model PRO-8A operating modes. Each of the six operating modes have specific operating frequencies (pulsed or continuous), and visible and infrared light combinations of LED operation. One visible LED is always on, regardless of mode selection, indicating power to the system is on. Every system is checked and tracked, by serial number, for correct diode performance, all six mode operation parameters as they relate to the specific diode, power output, and total operating time.

Figure 1:
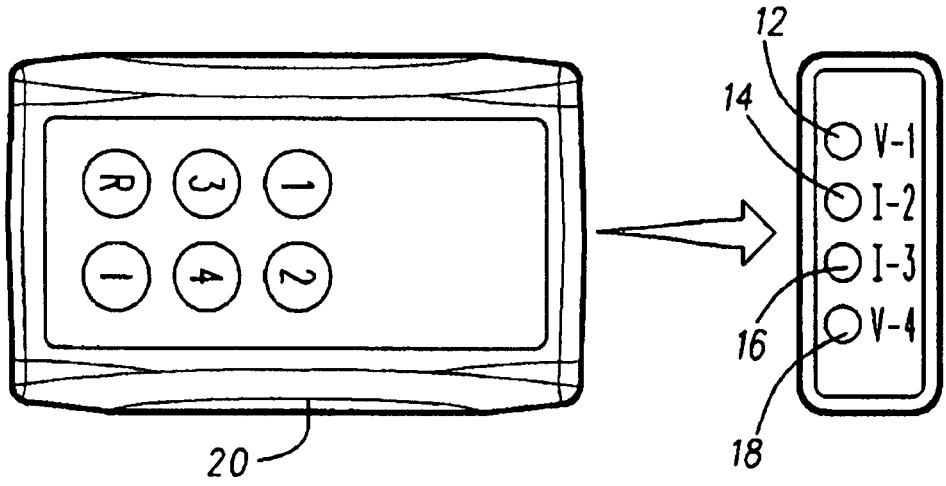
FIG. 1 is a top and end view of the GRT light apparatus.

As shown in FIGS. 1 and 2, the GRT LITE Model PRO-8A 10 includes operating controls consisting of six (6) user choice mode of operation controls and four (4) light emitting diodes (LEDs) 12, 14, 16, and 18 contained within housing 20. Two of the LEDs are in the visible light spectrum and flank two (2) LEDs which are in the infrared light spectrum. All four diodes transmit through a special red polymer lens 22; which is custom designed and manufactured from a non-absorption of light transmission acrylic material.

The "visible" LEDs (VI & V4) operate at a wavelength (A) of 628 nm (±5%)—measured.

The "Infrared" LEDs (1–2 & 13) operate at a wavelength (A) of 850 nm (±5%)—measured.

The six individual control switches allows for six separate modes of operation of the four LEDs.

Mode "1" a pulsed frequency mode with all four diodes operating at different frequencies with all automatically shutting off after 15 minutes:

VI 3.0 Hz 12 13.0 Hz 13 93.0 Hz

V4 7.0 Hz

Mode "2" a pulsed frequency mode with all four diodes operating at different frequencies with all automatically shutting off after 15 minutes:

VI 8.0 Hz 12 31.0 Hz 13 81.0 Hz

V4 38.0 Hz

Mode "3" a pulsed frequency mode with all four diodes operating at different frequencies with all automatically shutting off after 15 minutes:

VI 2.0 Hz 12 125.0 Hz 13 45.0 Hz

V4 10.0 Hz

Mode "4" a pulsed frequency mode with all four diodes operating at different frequencies with all automatically shutting off after 15 minutes:

V1 33.0 Hz 12 8.0 Hz 13 5.0 Hz

V4 22.0 Hz

Mode "R" a continuous mode at with both visible diodes continuously operating and both infrared diodes "Off," both automatically shutting off after 15 minutes:

V1 Continuous

12 Off

13 Off

V4 Continuous

Mode "I" a continuous mode at with both infrared diodes continuously operating, one visible diode is "Off," and 1 visible diode operating at 2.0 Hz and serves as a visual indicator the system is running, all three automatically shutting off after 15 minutes:

V1 Off

12 Continuous

13 Continuous

V4 2.0 Hz

The device is controlled using PROM technology. Once programmed, the "hard software" cannot be changed and/or altered and any changes and/or modifications would require a different chip. One visible LED is always on, regardless of mode selection, indicating power to the system is on.

The device can only be powered "ON" by depressing any of the six (6) control switches (buttons). The system can be powered "OFF" depressing any of the six (6) control switches (buttons), The specifications are as follows:

| | |
|---|---|
| Voltage: | Operating voltage: 1.6 v-4.6 v |
| Power: | 150 Ma |
| Safety: | Chassis-to-ground risk current 0 μA |

-continued

| | |
|---|---|
| Other: | FCC Standard - 47 CFR Part 15B<br>All Electrical Components Utilized Are UL ® Approved<br>System including batteries: 4.97 oz (141.1 gms) |
| Dimensions: | 4.344" × 2.376" × 1.100"<br>(110.338 mm × 60.198 mm × 27.94 mm) |
| Diodes: | Two Visible light LEDs<br>Two Infrared light LEDs |
| Power: | Maximum power output all diodes: ≦25.0 mwcm$^2$ |
| Wavelength: | Visible light LEDs - 628 nm (±5%) measured<br>Two Infrared light LEDs - 850 nm (±5%) measured |
| Temperature: | 10° C. to 40° C. operating, −20° C. to 50° C. storage. If system stored below 40° F., allow system to warm up to room temperature before use |
| Humidity: | 15% to 90% noncondensing |
| Altitude: | Operational capability beyond MMI standard of −500 to +5000 feet elevational barometric pressures |
| Impact: | Constructed to satisfy pre-shipment test standards of National Safe Transit Association, Document 2.4 |
| Battery: | Rechargeable batteries - 2 ea size "AA" NiMh - 2200 mAh - replaceable |
| VISIBLE DIODES: | |
| Diodes: | Two each light emitting diodes<br>Maximum power output per diode: ≦4.5 mw; diffuse beams |
| Wavelength: | 628 nm (±5%) measured |
| Safety: | Chassis-to-ground risk current during operation: 0 μA |
| Color: | Red |
| Temperature: | 10° C. to 40° C. operating, −20° C. to 50° C. storage. |
| Humidity: | 15% to 90% noncondensing. |
| INFRARED DIODES: | |
| Diodes: | Two each infrared light emitting diodes |
| Power: | Maximum power output per diode: ≦7.0 mw; Diffuse beams |
| Wavelength: | 850 nm (±5%) measured |
| Safety: | Chassis-to-ground risk current during operation: 0 μA |
| Color: | Clear |
| Temperature: | 10° C. to 40° C. operating, −20° C. to 50° C. storage |
| Humidity: | 15% to 90% noncondensing |
| LENS: | |
| Forming Temperature: | 300° F. (149° C.) |
| Refractive Index: | 1.49 |
| Light Transmission: | ≧98% |
| PH: | None |
| Color: | Red |
| Specific Gravity: | 1.1 to 1.2 |
| Composition: | P(MMA) Proprietary 99-100%<br>Methyl methacrylate <1% |
| Chemical Family: | Acrylic Copolymer |

COMPARISON TO PRIOR ART DEVICES

| Device | Manufacturer | Output Power* | Wave-length | Regulation Number | Product Code | Product Nomenclature |
|---|---|---|---|---|---|---|
| Present Invention Model 8-A | GRT Solutions, Inc. | ≦4.5 mwcm$^2$ | 628 nm | 21 CFR §890.5500 | NHN | Lamp, Infared |
| | | ≦7.0 mwcm$^2$ | 850 nm | | | |

* = per diode

Identification/Classification—21 CFR §890.5500—A device that emits energy at infrared frequencies (approximately 700 nanometers to 50,000 nanometers) to provide topical heating.

PRIOR ART DEVICE

| Device | Manufacturer | Wave-length | Regulation Number | Product Code | Product Nomen-clature |
|---|---|---|---|---|---|
| Erchonia PL3000 KL12580 | TUCO Innovations | 630 nm | 21 CFR §890.5500 | NHN | Lamp, Infared |

Identification/Classification—21 CFR §890.5500—A device that emits energy at infrared frequencies (approximately 700 nanometers to 50,000 nanometers) to provide topical heating.

| Device | Manufacturer | Wave-length | Regulation Number | Product Code | Product Nomen-clature |
|---|---|---|---|---|---|
| Excalibur Light Therapy System K041530 | TUCO Innovations | ≦5 $mwcm^2$ | 21 CFR §890.5500 | NHN | Lamp, Infared |

Identification/Classification:—21 CFR §890.5500 A device that emits energy at infrared frequencies (approximately 700 nanometers to 50,000 nanometers) to provide topical heating.

| Device | Manufacturer | Wave-length | Regulation Number | Product Code | Product Nomen-clature |
|---|---|---|---|---|---|
| Microlight 830 Laser System K010175 | Microlight Corporation of America | 830 nm | 21 CFR §890.5500 | NHN | Lamp, Infared |

Identification/Classification—21 CFR §890.5500—A device that emits energy at infared frequencies (approximately 700 nanometers to 50,000 nanometers) to provide topical heating.

| Device | Manufacturer | Wave-length | Regulation Number | Product Code | Product Nomen-clature |
|---|---|---|---|---|---|
| Acculasser PRO Low LLT Dev. K020657 | Acculasser, Inc. | 830 nm | 21 CFR §890.5500 | NHN | Lamp, Infared |

Identification/Classification—21 CFR §890.5500—A device that emits energy at infared frequencies (approximately 700 nanometers to 50,000 nanometers) to provide topical heating.

Software/Firmware—The system uses PROM technology employing firmware or what is also referred to as "hard software." The specific component CPU used can only be programmed one time and cannot be modified. Should any interruption of the program occur, the system will automatically shut off. The software provides a low battery indication and will not operate with any AC power source.

Personal Injury—There are no known risk for any type of personal injury that can be generated by the GRT LITE Model 8-A The system uses light emitting diodes (LEDs) as its energy source which have not proven to be damaging to human tissue. The Food and Drug Administration does not classify this device as a radiation emitting device and is considered a "non-significant risk" (NSR) device. In the infrared mode(s), the LEDs do not carry the high potential for injury to the eye as do infrared lasers used by other substantially equivalent devices. Regardless, the system still carries a clear "Warning Label" informing the user not to look directly into the light.

Operational Safety—There are no potential operational safety issues associated with the GRT LITE. This includes no known potential risk to the clinical operator and/or patient.

Regulatory Compliance Considerations

Food and Drug Administration (FDA)—The United States Food and Drug Administration (FDA) is the primary regulatory body covering the GRT LITE Model PRO-8A. Under the provisions of Title 21; U.S.C. and 21 Code of Federal Regulations (CER) both the corporation and the product must meet certain standards and comply with specific regulations:

Initial Registration of Device Establishment—This requirement was met by the filing of FDA Form 2891 on Jan. 27, 2005. It is the corporation's responsibility to report any changes and/or additions to the FDA. The FDA will issue an Owner/Operator Number to GRT Solutions, Inc. upon their completion of the processing of the form. (9070001)

Device Listing—All medical devices sold and distributed within the United States and its territories are required to be registered with the FDA. GRT Solutions, Inc. classification will be that of a "Repackager/Relabeler." This requirement was met by the filing of FDA Form 2892 on Jan. 27, 2005 (E214727).

FDA Approval to Market the GRT LITE Model PRO-8A—GRT Solutions, Inc. is required to file, and have approved by the FDA, what is called a "510(k) Application." This a notification of the corporation's intent to market the GRT LITE Model PRO-8A in the United States as a "substantially equivalent device" to other light therapy systems already approved to be marketed by the FDA. This filing/application must be approved by the FDA prior to marketing the GRT LITE Model PRO-8A. Although the user of the Model PRO-8A can decide which clinical protocol to utilize, GRT Solutions, Inc. is limited to presenting only the usage approved by the FDA in all its literature and/or operation instructions. We will be required to limit our marketing efforts to the FDA approved utilization applied for which is:

Adjunctive use in providing temporary relief of minor chronic neck and shoulder pain of musculoskeleral origin.

Adjunctive use in providing temporary relief of minor chronic pain from Carpal Tunnel Syndrome (CTS).

Medical Device User Fee Cover Sheet (MDUF)—This submission requires the payment of a fee to the FDA prior to the filing of the 510(k) application through FDA Form 3601. This requirement was met and carries the identification number of 017070-956733.

Good Manufacturing Practices—GRT Solutions, Inc. is required to adhere to what the FDA defines as "Good Manufacturing Practices." The FDA has the authority to inspect any or all GRT Solutions' owned entities involved in the manufacturing and distribution of the device. This includes, but is not limited to, quality control, testing, etc., etc. The itemization contained in the GRT Assembly Manual exceeds this requirement.

FDA Regulations (General)—The GRT LITE Model PRO-8AS is classified as a Class II Medical Device. It is regulated by the provisions of 21 CFR 890.5500 as an "infrared lamp." It also will be classified under a specific product code, i.e., "NHN," The device carries an "NSR" rating indicating it has "Non Significant Risk" to the user and/or patient.

Federal Communications Commission (FCC)—All commercial electronic devices (unintentional radio-frequency radiators) destined for sale in the United States that have clocks/oscillators that operate at a frequency of greater than 9 kHz and use digital techniques are regulated by the Federal Communications Commission (FCC) under Rules and Regulations, Title 47, Part 15 Subpart B. The GRT LITE Model PRO-8A design incorporates that consideration and meets the standard called for under Rules and Regulations, Title 47, Part 15 Subpart B.

State of California Department of Health Services/Food and Drug Branch—Since GRT Solutions, Inc. will operate in the state of California, the corporation is required to file a Medical Device Licensing Application with this entity and pay a licensing fee.

Occupational Safety and Health Administration (OSHA)—There are no anticipated risk of work-related injury (repetitive or otherwise) and/or illness to any GRT Solutions, Inc employee in the execution of their employee duties after the first 1,000 units are produced. Currently, the first 1,000 units call for a soldering station and will be implemented according to OSHA standards and requirements. The GRT Assembly Process Manual was developed to insure worker training and safety, and in the unlikely event of a work-related injury, GRT Solutions can comply with all OSHA reporting requirements.

In order to clarify how light affects the body, one needs to have an understanding of the basic physics involved. The three most relevant measurements for all systems (LED or Laser) are expressed in "wavelength"—"power output"—"frequency,"

Wavelength—This is the measurement of the light concentration arid is expressed in nanometers (nm). This metric measurement means each nanometer 900 equals I billionth of a meter or 1/25,400.000 of an inch. The technology involved with light therapy uses wavelengths from the visible spectrum of 380–760 nm to the near infrared spectrum which is greater than 760 nm. These are ranges/spectrums well away from the damaging spectrums of lower 600 wavelengths of ultraviolet, and the higher wavelengths of x-rays, gamma and cosmic rays. The GRT LITE's range is from 600 nm to 900 nm depending on the mode selected.

Power Output—This is the measurement of the light concentration expressed in watts per centimeter squared ($W/cm^2$). The GRT LITE operates at $\leqq 22 W/cm^2$ depending on the mode(s) selected.

Frequency—This is the measurement of the amount of time the light is activated and is expressed in "Hertz (Hz)" which is equal to one cycle per second. For example, if the system is operating at a frequency of 400 Hz that means the pulsed mode of that system has each second broken down into a total of 800 cycles. This translates to the system powering the diodes "ON - 400 times a second" and not powering the diodes, or "OFF - 400 times a second:"

To operate the GRT LITE requires ONLY two (2) very simple steps:

Step 1—Decide which of the six modes you want the GRT-LITE SYSTEM to operate in. The different modes are programmed at the factory and are set according to the following:

| Mode | Red D-1 Freq. | Infrared D-2 Freq. | Infrared D-3 Freq. | Red D-4 Freq. | Run Time |
|---|---|---|---|---|---|
| 1 | 3 Hz | 13 Hz | 93 Hz | 7 Hz | Auto OFF @ 15 min. |
| 2 | 8 Hz | 31 Hz | 81 Hz | 38 Hz | Auto OFF @ 15 min. |
| 3 | 2 Hz | 125 Hz | 45 Hz | 10 Hz | Auto OFF @ 15 min. |
| 4 | 33 Hz | 8 Hz | 5 Hz | 22 Hz | Auto OFF @ 15 min. |
| R | Continuous | Off | Off | Continuous | Auto OFF @ 15 min. |
| I | Off | Continuous | Continuous | 2 Hz | Auto OFF @ 15 min. |

Step 2—Depress the desired "Mode" button, for one-half second and execute the clinical procedure. Depress the "Mode" button, for one-half second to shut the system off Depressing any "Mode" button will turn the system off.

Note: The GRT-LITE will not operate if the battery levels are too low. We recommend changing batteries after 12–14 hours or two days use . . . whichever comes first.

Step 1—Patient Evaluation: A proper evaluation of the cervical and shoulder areas should consist of measurements of the patient's range of motion before and after treatment and the evaluation of the pain level.

Step 2—Depress the "Mode R" button on the GRT-LITE.

Step 3—Apply light starting in the cerebral region, at the top of the ear, illuminating the left cervical anterior and posterior muscles, working the light down into the left shoulder and torso anterior and posterior muscles. Keep the head of the GRT LITE ½" to ¾" from the skin's surface.

Step 4—Repeat Step 3 to right cervical shoulder and torso area.

Step 5—One minute of "Mode R" should be applied to right shoulder during passive external rotation of the shoulder. Cover the anterior muscles of the right shoulder (pectoralis group) with the patient's arm bent at the elbow.

NOTE: Whenever the word passive is used move the patient's appendage (head and/or shoulder) only as necessary to gain access with the light.

Step 6—One minute of "Mode R" applied to the right shoulder during passive adduction of patients right arm and shoulder. Cover the posterior muscles of the right shoulder.

Step 7—One minute of "Mode R" applied to the right cervical muscle and trapezius muscle during passive left lateral flexion of the cervical spine. Starting in the neutral position of the head, applies beams to the right cervical muscles and right trapezius muscles.

Step 8—One minute of "Mode R" to the right sternocleidomastold and scalene muscles during passive range of motion. Apply beams to the right sternocteidomastoid and scalenus muscles.

Step 9—Repeat step 5 to the left shoulder.

Step 10—Repeat step 6 to the left shoulder.

Step 11—Repeat step 7 to the left cervical spine.

Step 12—Repeat step 8 to the right cervical spine.

FDA Approved CTS Treatment Protocol

Step 1—Optional CTS Patient Application: General

Depress the "Mode I" button on the GRT-LITE.

Step 2—Patient Application: Optional Protocol Specific

The GRT-LITE can be used in either the pulsed or continuous mode to apply this protocol's required energy levels (joules).

Continuous Mode: Use "Mode I"

Figure 3:
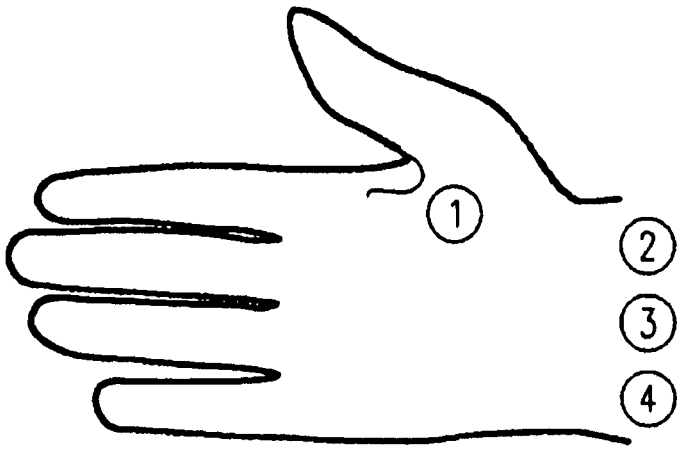
FIG. 3 is an illustration of a human hand indicating treatment points in accordance with the invention.

As shown in FIG. 3, apply light beams to the four treatment points 1, 2, 3 and 4 indicated in the picture to the right using the technique below. Use the flashing "red" beam as a placement guide.

Scan across the ulnar muscle between the Radial longitudinal crease and the proximal thumb joint.

Direct beams on the radial side of wrist at the proximal wrist crease.

Direct beams to the middle of the wrist at the proximal wrist crease across the carpal ligament.

Direct beams to the ulnar side of the wrist at the proximal crease across the carpal ligament.

Repeat the direction of the beams to the ulnar side of the wrist at the proximal crease across the carpal ligament.

Step 3—Re-evaluate Patient

Following the treatment the practitioner can re-evaluate the patients wrist range of motion noting any changes. They can also note any changes in patient's ability to tolerate pain.

The GRT LITE has been designed so that there is no maintenance required by the user other than keeping the GRT LITE clean, stored in the proper environment, and battery replacement (see Quick Reference Card).

The designed operating life of each diode is in excess of 100,000 clinical applications to minimize failure during the life of the product. Any rare failure of the (visible red diodes Dl or 04) will be obvious, as they will not illuminate when the system is powered on. If you suspect one of the (invisible infrared diodes 02 or 03) has inexplicably failed you can check them performing the following test procedures:

Using a standard digital camera with an LCD screen, or a digital camcorder, depress the "I" control and look through the viewer at the top of the system. Both 02 and 03 will emit a "bright" glow; 04 will flash two times per second. This verifies the GRT LITE is working properly.

All repair and/or service to GRT LITE must be done by an authorized GRT SOLUTIONS facility or service center. Any disassembling of the system immediately voids the warranty.

Dirt, dust, moisture and oils from the human body may settle on the system. These can distort the beams by clouding the lenses and may affect clinical performance. Regardless, the GRT LITE . . . can not be sterilized by any liquid or autoclave method Routine Cleaning The user may remove dirt, dust and oils by wiping the GRT LITE clean with a dry cloth. Cleaning should be limited to wiping the GRT LITE clean. The red lens covering the four diodes should be cleaned using the following steps:

Blow the system clean using a compressed air aerosol the type used to clean computers and electronics.

Wipe the red lens with a standard alcohol swab.

The lens can be cleaned using a Q-Tip™ type cotton swab dipped in alcohol.

Repeat aerosol spray making sure system is completely dry.

Inspect the unit before each use or after changing the batteries. Clean system at least weekly after every five patients.

The invention claimed is:

1. Therapeutic apparatus comprising:

a housing a plurality of light emitting diodes within said housing;

a transparent lens covering said light emitting diodes; and a control circuit having an embedded program for selectively activating and deactivating said light emitting diodes;

said plurality of light emitting diodes comprising at least one visible light emitting diode and at least one infrared diode transmitting in a frequency range of between 845 to 855 nanometers and pulsing at a range of less than 125 Hz.

* * * * *